United States Patent [19]

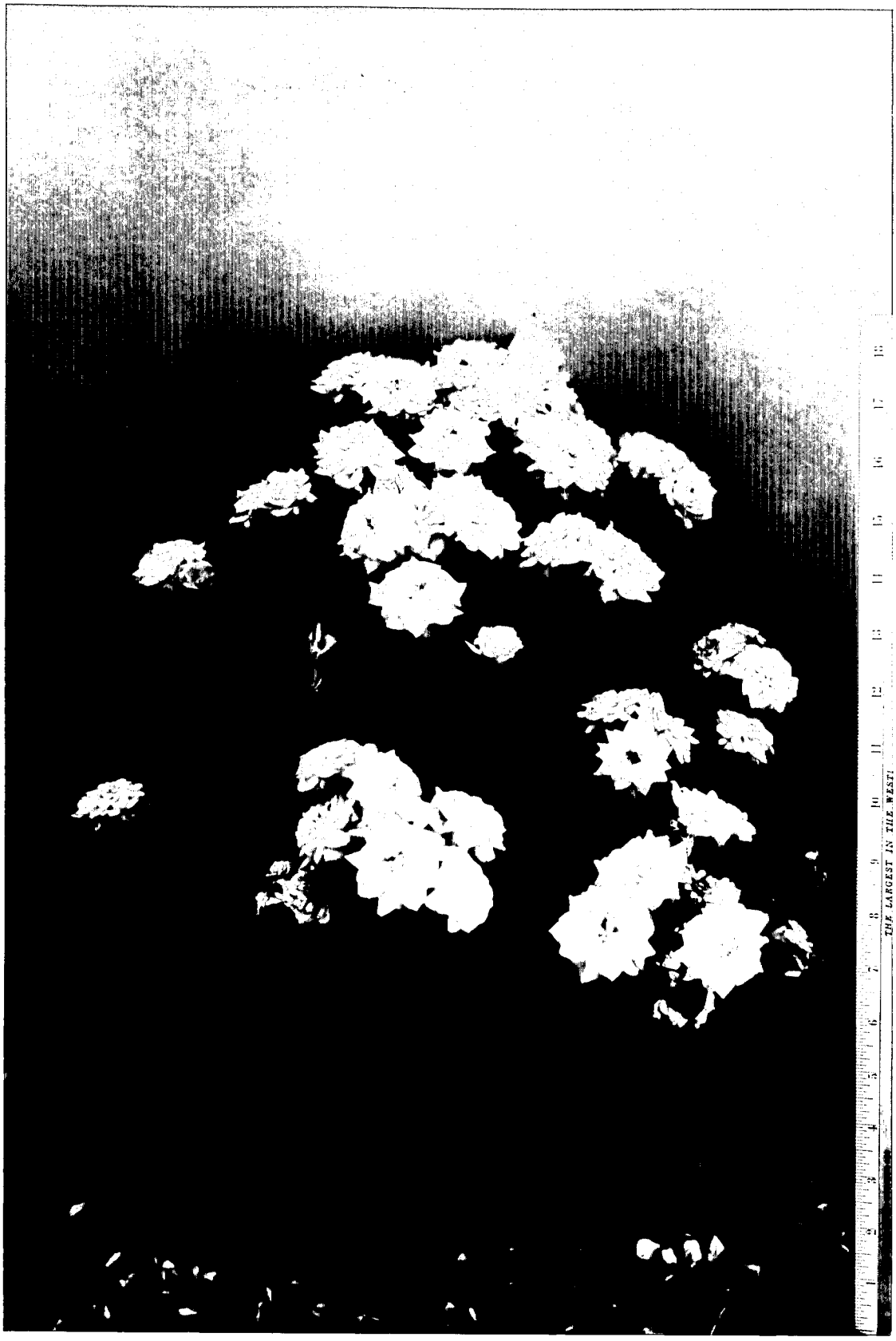
THE LARGEST IN THE WEST!

Warriner

[11] Patent Number: Plant 5,578

[45] Date of Patent: Oct. 29, 1985

[54] ROSE PLANT JACOUCH

[75] Inventor: William A. Warriner, Tustin, Calif.

[73] Assignee: Jackson & Perkins Company, Medford, Oreg.

[21] Appl. No.: 557,199

[22] Filed: Dec. 2, 1983

[51] Int. Cl.[4] ..... A01H 5/00

[52] U.S. Cl. ..... Plt./9

[58] Field of Search ..... Plt./9

*Primary Examiner*—James R. Feyrer

*Attorney, Agent, or Firm*—Klarquist, Sparkman, Campbell, Leigh & Whinston

[57] ABSTRACT

A miniature rose variety having the characteristic miniature plant size and growth habit, blooms in clusters, salmon pink colored blooms having very stiff petals, little or no fragrance, and high resistance to rose powdery mildew.

1 Drawing Figure

This present invention relates to a new and distinct variety of rose plant of the miniature class which was originated by me by crossing the variety Bridal Pink, U.S. Plant Pat. No. 2,851, with the variety Fire Princess, U.S. Plant Pat. No. 3,084.

The primary objective of this breeding was to produce a new rose variety combining the miniature characteristics of Fire Princess with certain characteristics of Bridal Pink. This objective was substantially achieved along with other desirable improvements as evidenced by the following unique combination of characteristics which are outstanding in the new variety and which distinguish it from its parents, as well as from all other varieties of which I am aware:

1. Plant size and habit of the miniature class.
2. Blooms in clusters.
3. Bloom color of R.H.S. Red Group 48B, commonly referred to as salmon pink.
4. Very stiff petal substance.
5. Little or no fragrance.
6. High resistance to rose powdery mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Bridal Pink, U.S. Plant Pat. No. 2,851.

*Pollen parent.*—Fire Princess, U.S. Plant Pat. No. 3,084.

Classification:

*Botanical.*—Rosa hybrid.

*Commercial.*—Miniature.

FLOWER

Observations made from specimens grown at Irvine, Calif. in October.

Blooming habit: Continuous.

Bud:

*Size.*—$\frac{1}{2}''$ when petals start to unfurl.

*Form.*—Pointed ovoid.

*Color.*—When sepals first divide, Red Group 48A. When half blown; upper side of petals Red Group 48B; lower side of petals Red Group 48B.

*Sepals.*—Color: Outer surface Green 138A, surface scattered with stipitate glands. Three appendaged sepals lightly appendaged. Two unappendaged sepals hairy edged.

*Receptacle.*—Color: Green 138A. Shape: Funnel. Size: Large. Surface: Slightly glandular.

*Peduncle.*—Length: Short. Surface: Slightly glandular. Color: Medium green. Strength: Stiff, erect.

*Opening.*—Petals fold out, center depressed in half-open stage.

Bloom:

*Size.*—Small. Average open size: $1\frac{1}{2}''$.

*Borne.*—In clusters, rounded.

*Stems.*—Short, strong.

*Form.*—When first open, high centered. Permanence: Retains its form to the end.

*Petalage.*—Number of petals under normal conditions: 25-30.

*Color.*—Center of flower: Upper side of petals Red Group 48C; reverse side of petals Red Group 48C; base of petals have large area near white. General tonality from a distance: Red Group 48C.

*Variegations.*—None.

*Discoloration.*—General tonality at end of first day: No change. Fourth or fifth day: Petals fade to Red Group 48D or lighter before dropping.

*Fragrance.*—None.

Petals:

*Texture.*—Thick.

*Shape.*—Narrow, oval, pointed, nearly lanceolate.

*Form.*—Edges slightly quilled.

*Arrangement.*—Imbricated. Petaloids in center: few, large.

*Persistence.*—Drop off cleanly.

*Lastingness.*—On the plant, very long. As cut flower, very long.

Reproductive parts:

*Anthers.*—Large, many. Color: Yellow. Arrangement: Regular around styles.

*Filaments.*—Color: Pale yellow.

*Pollen.*—Lemon yellow.

*Styles.*—Color: Rose red.

*Stigmas.*—Color; White.

PLANT

Form: Bush.

Growth: Vigorous, dewarf, attaining normal height of 18" to 24".

Foliage: Number of leaflets on normal mid-stem leaves: 5 or 7.

*Size.*—Medium.

*Quantity.*—Normal.

*Color.*—New foliage: Red Purple 59A quickly turning green upon unfolding. Old foliage: Medium green (ordinary dictionary term).

Leaflets:

*Shape.*—Oval pointed.

*Texture.*—Leathery on upper side.

*Edge.*—Serrated.

*Serration.*—Single, small.

*Petiole.*—Rachis: Color: Green. Underside: Prickles.

*Stipules.*—Long, bearded.

*Disease resistance.*—Resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base: ordinary. On laterals from stalk: ordinary.

*Form.*—Long, hooked slightly downward.

*Color when young.*—Green and red.

*Position.*—Irregular.

Small Prickles:

*Quantity.*—On main stalks: few. On laterals: few.

*Color.*—Brown.

I claim:

1. A new and distinct variety of rose plant of the miniature class, substantially as herein shown and described, characterized particularly as to novelty by the unique combination of its clusters of salmon pink blooms, stiff petal substance, lack of fragrance and resistance to rose powdery mildew.

* * * * *